(12) United States Patent
Brooker et al.

(10) Patent No.: US 6,487,895 B2
(45) Date of Patent: *Dec. 3, 2002

(54) CORROSION MONITORING SYSTEM

(75) Inventors: Donald Duane Brooker, Hopewell Junction, NY (US); Michael Edward Fahrion, Houston; Byron Von Klock, Beaumont, both of TX (US); George Neal Richter, San Marino, CA (US)

(73) Assignee: Texaco Development Corporation, San Ramon, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/996,424

(22) Filed: Nov. 20, 2001

(65) Prior Publication Data

US 2002/0033042 A1 Mar. 21, 2002

Related U.S. Application Data

(63) Continuation of application No. 09/214,814, filed as application No. PCT/US97/12050 on Jul. 11, 1997, which is a continuation of application No. 08/891,120, filed on Jul. 10, 1997, now Pat. No. 5,948,971.
(60) Provisional application No. 60/021,890, filed on Jul. 17, 1996.

(51) Int. Cl.⁷ ............................................... G01N 17/00
(52) U.S. Cl. ......................................................... 73/86
(58) Field of Search .................... 73/86, 866.5; 116/208

(56) References Cited

U.S. PATENT DOCUMENTS

3,621,810 A * 11/1971 Zuck, Jr. ........................ 73/86
4,389,877 A    6/1983 Lacey
5,181,536 A *  1/1993 Argyle et al. ................... 73/86
5,297,940 A *  3/1994 Buse .............................. 73/86

FOREIGN PATENT DOCUMENTS

JP          8-15112       6/1994

* cited by examiner

Primary Examiner—Robert Raevis
(74) Attorney, Agent, or Firm—Morris N. Reinisch; Frank C. Turner; Rodman & Rodman

(57) ABSTRACT

A corrosion sensor for sensing corrosion in a pipeline. The sensor includes a housing and a device for joining the housing to a wall of an enclosure that receives a fluid. The sensor also includes a rupture member which extends across a portion of the housing to define a sealed chamber in the housing. The rupture member, upon rupture, provides an opening to the sealed chamber. The rupture member is formed of a material and thickness such that the rupture member will fail from corrosion before the enclosure wall will fail from corrosion. The rupture member is arranged such that fluid received in the enclosure can contact the rupture member. The sensor also includes a sensory device which is connected to the housing at the sealed chamber to signal a rupture condition of the rupture member when the sealed chamber opens.

10 Claims, 1 Drawing Sheet

CORROSION MONITORING SYSTEM

This application is a continuation of U.S. patent application Ser. No. 09/214,814, now U.S. Pat. No. 6,367,315 which is a §371 of PCT/US97/12050 filed Jul. 11, 1997 which is a continuation of U.S. patent application Ser. No. 08/891,120 filed Jul. 10, 1997, now U.S. Pat. No. 5,948,971, which is a continuation of U.S. Provisional Application No. 60/021,890 filed Jul. 17, 1996.

BACKGROUND OF THE INVENTION

This invention relates to a corrosion sensing device and more particularly to a corrosion sensor that can be positioned at a desired location in a pipeline system to detect corrosion in the pipeline system.

Pipeline corrosion is generally a hidden problem that often cannot be controlled in many industrial settings. In the chemical industry, corrosion activity can limit equipment life and threaten the reliability of industrial installations. Useful materials in process fluids can cause corrosion of the apparatus used to handle such fluids resulting in a need to curtail operations or shut down a processing system. Correcting the effects of corrosion can thus lead to high maintenance costs. Since it is not often feasible to control corrosion, the effects of corrosion are usually dealt with by removing and replacing the afflicted structure at an estimated stage of corrosion damage.

Thus, one known remedy for dealing with pipeline corrosion is to replace sections of a pipeline at predetermined time intervals rather than risk pipeline rupture and system shutdowns. However, this procedure can be unduly expensive if pipeline is replaced too soon when it still has substantial useful life. Therefore, one of the problems in dealing with pipeline corrosion is accurately determining the optimum time to replace a pipeline.

If information on the extent of corrosion activity is obtainable before significant damage occurs, remedial measures can be taken to repair process equipment before the corrosion activity leads to equipment failure. Thus, an effective corrosion monitoring program typically begins with obtaining information on the extent of corrosion damage or corrosion activity occurring in a particular installation. With regard to pipeline corrosion, a variety of different techniques have been used for determining the amount of corrosion damage or corrosion activity that has occurred in a pipeline used for conveying process fluids.

U.S. Pat. Nos. 4,328,462, 4,768,373 and 5,571,955 disclose the use of probes which are inserted into containers or pipes holding a fluid that causes the pipe or container to corrode. The probes react to the corrosive influence of the fluid in a known correlation to the corrosive response of the material forming the container or pipe. However, the pressures and temperatures often associated with chemical processes severely limit the opportunity to install and remove such probes from the container or pipe, thus limiting access to information on corrosion activity that they are designed to provide.

Other known techniques for determining corrosion activity of process fluids rely on sampling of the process fluids in a processing structure in order to detect corrosive agents or corrosion by-products correlated to corrosion activity. However, sample testing is often time consuming and can thus impose considerable delay between the time of sampling and the reception of analytical results of corrosion tests.

U.S. Pat. No. 4,389,877 describes a system to monitor the amount of erosion taking place within a pipe. Notches are formed in the wall of the pipe to provide an area of reduced strength. A hollow, sealed casing is built around the pipe at the point of reduced strength to provide a leak-tight chamber. A conduit from the hollow, sealed casing is connected to an outside sensing device to monitor pressure changes in the casing. A predetermined pressure change will indicate when a pipe failure occurs at the portion of reduced strength. However, the need to provide areas of reduced strength and a hollow casing around the areas of reduced strength with special sealing material and a sealing collar make it difficult and expensive to employ the '877 system. Moreover, the '877 system allows monitoring only of the pipe area that is notched and sealed with a casing. Thus, areas of the pipeline system which are not easily accessed cannot be monitored. Consequently, remote areas of a pipeline system that might be vulnerable to corrosion failure do not receive adequate monitoring.

It is therefore desirable to provide a reliable method and means for detecting corrosion anywhere in a pipeline system, which means is easily connected to a pipe or sections of pipe and can be used under conditions of high temperature and/or pressure.

OBJECTS AND SUMMARY OF THE INVENTION

One of several objects of the invention is the provision of a novel method and means of accurately detecting corrosion anywhere in a pipeline system. Another object of the invention is the provision of a novel method and means of accurately detecting when corrosion in a pipeline system has reached a predetermined level. Another object of the invention is the provision of a novel method and means of detecting corrosion of a pipeline system without the need to sample the fluid or to insert a probe into the fluid. Yet another object of the invention is the provision of a novel method and means of accurately detecting corrosion of a pipeline system under conditions of high temperature and/or high pressure. Yet still another object of the invention is the provision of a novel method and means of securing a corrosion detector in a pipe without altering the existing pipe structure.

In accordance with the present invention, a corrosion sensor is provided which includes a housing and a device for joining the housing to a wall of an enclosure that receives a fluid. The sensor also includes a rupture member which extends across a portion of the housing to define a sealed chamber in the housing that is maintained at a predetermined pressure. The rupture member is formed of a material that is structured to fail from corrosion before the enclosure wall is subject to corrosion failure. The rupture member is joined to the enclosure such that fluid received in the enclosure can contact the rupture member under similar conditions in which the fluid contacts the wall of the enclosure. The rupture member, upon rupture due to corrosion, provides an opening to the sealed chamber and thus changes the pressure conditions inside the chamber. The corrosion sensor also includes a sensing system which is connected to the housing at the sealed chamber to signal a rupture condition of the rupture member when the sealed chamber opens. The sensing system includes a pressure sensor and signaling device that cooperates with the pressure sensor to provide a signal in response to predetermined pressure levels measured by the pressure sensor.

In one embodiment of the invention, the rupture member includes a rupturable section which comprises an area of predetermined, reduced thickness relative to the thickness of the rupture member.

The invention also provides a method of sensing corrosion in a pipeline system. The method includes conveying a fluid within a pipeline system that includes at least one wall formed of a material that is vulnerable to corrosion. The method further includes joining a sensor to the pipeline system such that fluid flows through one section of the pipeline system and past the sensor to another section of the pipeline system. The method also includes providing a rupture member in the sensor to form a sealed chamber and arranging the rupture member such that fluid flowing through the one pipe contacts the rupture member. The method further includes forming the rupture member of a material structured to fail from corrosion before the wall of the pipeline system fails from corrosion. The method also includes providing a signal when the rupture member ruptures.

DETAILED DESCRIPTION

Figure 1:
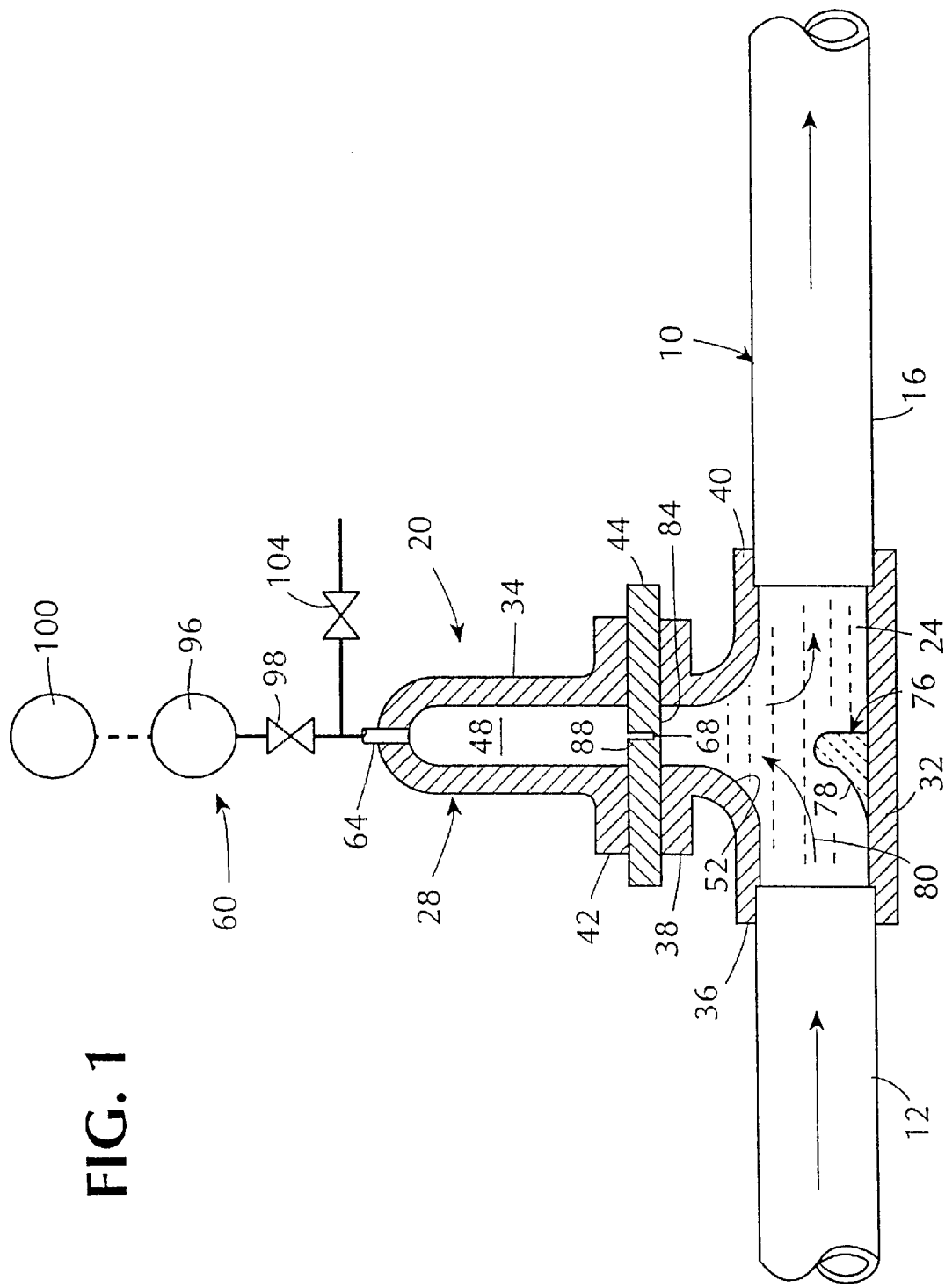
FIG. 1 is an upright, sectional view of a system for detecting corrosion in a pipeline, incorporating one embodiment of the invention.

Referring to FIG. 1, a pipe system 10 includes a first pipe section 12 and a second pipe section 16 joined by a corrosion sensor 20. The pipe sections 12 and 16 are of a known construction and can be formed from a metal such as stainless steel 304. The pipes 12 and 16 convey a process fluid 24 of low pH value in the range of zero to 5 such as acidic water. The process fluid 24 can have a temperature of approximately 450 degrees F. and a pressure of approximately 1200 p.s.i.g. The corrosion sensor 20 includes a housing 28 having a T-section 32 and a bell section 34 joined together about a rupture member 44. The housing 28 can be formed from the same material as the pipes 12 and 16.

The T-section 32 has opposite pipe joining ends 36 and 40 for connection with the first and second pipe sections 12 and 16 respectively in any suitable, known manner, such as welding with or without threading. The T-section 32 also includes a neck portion 52 intermediate the pipe joining ends 36 and 40 which neck portion 52 terminates in a flange 38. In some instances, under relatively low fluid flow rates, a flow deflector 76, preferably made of a non-corrodible material, such as ceramic, can be mounted in the T-section 32 between the ends 36 and 40 and opposite the rupture member 44. The flow deflector 76 has a flow deflection surface 78 to direct the flow of the process fluid 24, as indicated by arrow 80 into the neck portion 52 against the rupture member 44. Thus, a portion of the fluid 24 passing through the pipe sections 12 and 16 can be directed toward the rupture member 44 by the flow deflector 76.

The rupture member 44 includes a fluid exposed surface 84 which can be disposed above the fluid flow path and over the fluid deflector 76. The pipes 12 and 16 can have an inner diameter of approximately six inches and a wall thickness of approximately one to two inches. The fluid exposed surface 84 of the rupture member 44 can be flush mounted in any suitable known manner with the inner surface of the pipe or recessed approximately one to two inches from the inside diameter of the pipe joining ends 36 and 40. Upward disposition of the rupture member 44 when the fluid exposed surface 84 is recessed helps to avoid accumulation of sediment or other debris from the process fluid 24 on the fluid exposed surface 84. Sediment accumulation on the exposed surface 84 of the rupture member 44 is likely to occur if the recessed rupture member 44 is located under the fluid flow path. The rupture member 44 can be formed of a metal similar to the metal of the pipe sections 12 and 16, but of lesser thickness such as ½ the wall thickness of the pipe section 12 and 16. If desired, the rupture member can be formed from a metal, such as carbon steel, which corrodes at a faster rate than the pipes 12 and 16.

When the rupture member 44 is of the same material as the pipe sections 12 and 16 and half as thick as the pipes 12 and 16, failure of the rupture member will occur approximately twice as quickly as the pipes 12 and 16. If the rupture member is formed of carbon steel of equal thickness as the pipes 12 and 16, the rupture member 44 is also likely to fail in a quicker time than it takes for the pipe to fail. The relative time difference between rupture of the rupture member 44 and rupture of the pipe sections 12 and 16 can be predetermined based on the specific characteristics of the fluid medium that is conveyed by the pipe.

If desired, the rupture member 44 can be formed with a rupturable section 68 of reduced wall thickness with respect to the remainder of the rupture member 44. The rupturable section 68 can, for example, be formed as the remaining thickness below a small diameter, blind hole 88 which can be drilled or bored into the rupture member 44. The rupturable section 68 can, for example, be formed with a thickness of one half the thickness of the pipes 12 and 16 if the rupture member is formed of stainless steel.

The bell section 34 defines a chamber 48 having an open end with a flange 42. The rupture member 44 is sandwiched between the T-section flange 38 and the bell section flange 42 which are joined together in any suitable, known manner to form a leak tight joint. The chamber 48 is thus sealed and preferably maintained at ambient pressure by a pressure bleed valve 104.

A sensing device or sensor 60 for signaling a rupture condition of the rupturable section 68 of the rupture member 44 is joined to the bell section 34 by a conduit 64 that communicates with the chamber 48. The sensor 60 includes a conventional pressure valve 98 on the conduit 64 that communicates with a pressure detector or pressure indicator 96. A conventional alarm or signal system 100 communicates with the pressure detector 96.

In operation of the pipe system 10 and the corrosion sensor 20, the process fluid 24 is conveyed through the pipes 12 and 16. The flow deflector 76, which is optional, especially in flow systems under relatively high pressure such as 1200 p.s.i.g., helps direct the process fluid 24 into the neck portion 52 of the T-section 32 and against the rupture member 44. After a predetermined time, the pipes 12 and 16 will experience corrosion as a result of exposure to the process fluid 24. The flow deflector 76 is usually omitted if there will be relatively heavy particulate matter in the liquid flowing through the pipes 12 and 16 such as ash, corrosion scale and soot.

The rupture member 44, whether formed of the same material or of a different material than the pipes 12 and 16, is arranged to experience corrosion failure before the pipes 12 and 16. The rupture member 44 can thus be structured to fail at a predetermined fraction, e.g. one-half, of the anticipated life of the pipeline. Thus, when the rupture member 44 fails, a predetermined amount of pipe life remains before it will also fail.

Rupture of the rupture member 44 permits the fluid 24, usually under high pressure, to enter the corrosion chamber 48. The pressure detector 96 detects a rupture condition by sensing a change in the ambient pressure in the chamber 48 which is now at the pressure of the pipe system 10. The pressure detector 96 activates the alarm 100 at a predetermined pressure to indicate that a failure of the rupture member 44 has occurred.

Since the rupture member 44 is located between the pipe sections 12 and 16 close to the flow path of fluid in the pipe sections 12 and 16, the flow conditions experienced by the rupture member 44 are substantially the same as the flow conditions in the pipe sections 12 and 16. Because of the proximity of the rupture member 44 to the pipe sections 12 and 16, corrosion of the rupture member 44 is representative of the corrosion affecting the pipe sections 12 and 16. Since the corrosion sensor 20 can be conveniently installed in a pipeline, it is possible to use the corrosion sensor 20 to detect corrosion at substantially all sections of a pipeline.

As various changes can be made in the above constructions and method without departing from the scope of the invention, it is intended that all matter contained in the above description or shown in the accompanying drawing shall be interpreted as illustrative and not in a limiting sense.

What is claimed is:

1. A method for sensing corrosion in a rigid pipeline system, comprising:

conveying a fluid within a rigid pipeline system having a plurality of rigid pipes, said pipeline system having at least one rigid wall formed from a corrodible material;

joining a rigid sensor housing directly to one of said rigid pipes in the pipeline system without perforating or forming an opening in any rigid wall portion of the pipeline system and without reducing the wall thickness of any of the rigid pipes in the pipeline system such that fluid flowing through said one rigid pipe of the pipeline system also flows directly from said one rigid pipe through said sensor;

providing a rupture member across a portion of said sensor to form a sealed chamber, and arranging the rupture member on the sensor such that fluid flowing through said one rigid pipe contacts said rupture member;

forming said rupture member of a material and thickness that will enable said rupture member to fail from corrosion before said one rigid wall in the pipeline system fails from corrosion; and signaling a rupture condition of said rupture member upon rupture of said rupture member by detecting the pressure in the sealed chamber and generating a signal when a predetermined pressure level in excess of ambient pressure conditions is detected in the sealed chamber as a result of the rupturing of the rupture member that causes the sealed chamber to open to the fluid flowing through said one rigid pipe.

2. The method of claim 1, including recessing the rupture member from the one wall.

3. The method of claim 1, including forming the rupture member of metal.

4. The method of claim 1, including forming the rupture member of a material that corrodes at a faster rate than the corrodible wall of the pipeline.

5. The method of claim 1, including using a sensory device with a pressure indicator and an alarm to signal a rupture condition.

6. The method of claim 1, including joining the rigid sensor housing to an end portion of one of said rigid pipes.

7. The method of claim 6 including joining the rigid sensor housing to confronting end portions of two of said rigid pipes such that fluid flow within the pipeline system flows sequentially from one of said two rigid pipes through the sensor housing and through the other of said two rigid pipes.

8. The method of claim 1, including recessing the rupture member from the one wall and forming the rupture member with a rupturable section having an area of a predetermined, reduced thickness with respect to the overall thickness of the rupture member.

9. A method for sensing corrosion in a rigid pipeline system, comprising:

conveying a fluid within a rigid pipeline system having a plurality of rigid pipes, that are joined end to end to form the pipeline system, said pipeline system having at least one rigid wall formed from a corrodible material;

joining a rigid sensor housing directly to one end of one of said rigid pipes in the pipeline system without perforating or forming an opening in any rigid wall portion of the pipeline system and without reducing the wall thickness of any of the rigid pipes in the pipeline system such that fluid flowing through said one rigid pipe of the pipeline system also flows directly from said one rigid pipe through said sensor;

providing a rupture member across a portion of said sensor to form a sealed chamber, and arranging the rupture member on the sensor such that fluid flowing through said one rigid pipe contacts said rupture member;

forming said rupture member of a material and thickness that will enable said rupture member to fail from corrosion before said one rigid wall in the pipeline system fails from corrosion; and signaling a rupture condition of said rupture member upon rupture of said rupture member by detecting the pressure in the sealed chamber and generating a signal when a predetermined pressure level in excess of ambient pressure conditions is detected in the sealed chamber as a result of the rupturing of the rupture member that causes the sealed chamber to open to the fluid flowing through said one rigid pipe.

10. A method for sensing corrosion in a rigid pipeline system, comprising:

conveying a fluid within a rigid pipeline system having a plurality of rigid pipes, that are joined end to end to form the pipeline system, said pipeline system having at least one rigid wall formed from a corrodible material;

joining a rigid sensor housing directly to confronting ends of two of the rigid pipes in the pipeline system by assembling the sensor housing to the confronting ends of the rigid pipes without perforating or forming an opening in any rigid wall portion of the pipeline system and without reducing the wall thickness of any of the rigid pipes in the pipeline system such that fluid flowing through said one rigid pipe of the pipeline system also flows directly from said one rigid pipe through said sensor;

providing a rupture member across a portion of said sensor to form a sealed chamber, and arranging the rupture member on the sensor such that fluid flowing through said one rigid pipe contacts said rupture member;

forming said rupture member of a material and thickness that will enable said rupture member to fail from corrosion before said rigid one wall in the pipeline system fails from corrosion; and signaling a rupture condition of said rupture member upon rupture of said rupture member by detecting the pressure in the sealed chamber and generating a signal when a predetermined pressure level in excess of ambient pressure conditions is detected in the sealed chamber as a result of the rupturing of the rupture member that causes the sealed chamber to open to the fluid flowing through said one rigid pipe.

* * * * *